United States Patent
Kwon et al.

(12) 
(10) Patent No.: US 6,387,948 B1
(45) Date of Patent: May 14, 2002

(54) 8-ACETYLARTEMINOLIDE AND PROCESS FOR PREPARING SAME

(75) Inventors: Byoung-Mog Kwon; Kwang-Hee Son; Ha-Won Jeong; Seung-Ho Lee; Mi-Young Han, all of Daejeon; Hyun-Mi Kang, Chungcheongbuk-do; Hyae-Kyeong Kim, Daejeon; Soo-Ik Chang, Chungcheongbuk-do, all of (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 09/596,363

(22) Filed: Jun. 17, 2000

(30) Foreign Application Priority Data

Mar. 22, 2000 (KR) .............................. 00-14469

(51) Int. Cl.[7] .............................. A61K 31/343
(52) U.S. Cl. .................. 514/462; 549/298; 549/264; 549/265
(58) Field of Search ............... 549/298, 264, 549/265; 514/462

(56) References Cited

PUBLICATIONS

Nancy E. Kohl et al., Selective Inhibition of Ras–Dependent Transformation by a Farnesyltransferase Inhibitor, *Science*, vol. 260, Jun. 25, 1993, pp. 1934–1937.

Yuval Reiss et al., Inhibition of Purified P21$^{RAS}$ Farnesyl:Protein Transferase by Cysaax Tetrapeptides, *Cell*, vol. 62, 81–88, Jul. 13, 1990.

Jackson B. Gibbs et al., Pharmaceutical Research in Molecular Oncology, *Cell*, vol. 79, 193–198, Oct. 1994.

Jack L. Arbiser et al., Oncogenic H–Ras Stimulates Tumor Angiogenesis by Two Distinct Pathways, *Proc. Natl. acad. Sci. USA*, vol. 94, pp. 861–866, Feb. 1997, Cell Biology.

John K. Buolamwini, Novel Anticancer Drug Discovery, *Current Opinion in Chemical Biology*, 1999, 3:500–509.

Jakupovic et al, Phytochemistry, 26(10), pp. 2777–2779, 1987.*

* cited by examiner

*Primary Examiner*—Ba K. Trinh
(74) *Attorney, Agent, or Firm*—Rosenman & Colin, LLP.

(57) ABSTRACT

8-Acetylarteminolide of the formula (I) having inhibitory activities against farnesyl-protein transferase(FPTase), a progression of the cell cycle and angiogenesis may be useful for the prevention and treatment of various cancers and angiogenesis-related diseases:

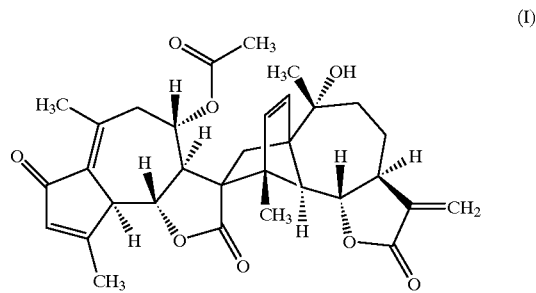

1 Claim, 3 Drawing Sheets

8-ACETYLARTEMINOLIDE AND PROCESS FOR PREPARING SAME

FIELD OF THE INVENTION

The present invention relates to a novel arteminolide compound obtained from the flower of *Artemisia sylvatica* MAXIMOWICZ and designated 8-acetylarteminolide which is effective in inhibiting farnesyl-protein transferase ("FPTase"), a progression of the cell cycle and angiogenesis; to a process for the preparation thereof; and to a pharmaceutical composition containing same.

BACKGROUND OF THE INVENTION

It has been found that ras oncogene, a well-known oncogenic gene, is activated in about 30% of human cancer cells. In order to transform cells, the Ras protein must bind to the plasma membrane, and for this binding to occur, a farnesyl group must be attached to the C-terminus thereof. Thus, it has been expected that inhibition of the FPTase involved in such farnesylation step could repress the expression of ras oncogene.

The Ras protein produced by the expression of ras oncogene has a molecular weight of 21 kDa and consists of 188–189 amino acid residues. It is capable of binding with guanine nucleotides (GDP and GTP) to act as a signal transmitting agent to growth factors. The ras oncogene, which is the first oncogenic gene found in human carcinomas, is classified into harvey-ras (H-ras), kirsten-ras (K-ras) and N-ras. More than 30% of the human cancer cells examined were found to contain mutated ras genes which produce Ras proteins (H-Ras, K-Ras and N-Ras) of abnormal biological activities. In particular, mutated ras genes have been found in 90% of exocrine pancreatic carcinoma, 50% of colon carcinoma and 50% of lung cancer cases (M. Barbacid, *Ann. Rev. Biochem.*, 56, 779(1987)).

Normal Ras proteins are involved in the regulation of growth and division in animal cells, and like other G-proteins, must bind with GTP to become activated or "switched on" as a signal transmitting agent, while it becomes deactivated or "switched off" when the bound GTP thereto gets hydrolyzed to GDP (G. Bollag, *Ann. Rev. Cell Biol.*, 7, 601(1991)).

Biochemical and structural studies have suggested that after binding with GTP, the Ras protein must be localized in the plasma membrane in order to perform its intended biological function. For the Ras protein to become functional by attaching itself to the plasma membrane, the inactive precursor produced in the cytoplasm protein must bind with lipids, more specifically, with isoprenoid derivatives generated in the steroid biosynthesis, through a series of reactions called post-translational modifications. Such lipid binding reaction, i.e., farnesylation, occurs at the cysteine residue site of the C-terminus of Ras protein containing a sequence motif expressed by CAAX, wherein C is cysteine, A is an aliphatic amino acid and X is Ser, Ala, Met or Glu, which serves as the recognition site for farnesyl-protein transferase (FPTase).

The above mentioned binding of a farnesyl group to the cysteine residue of the Ras C-terminus represents the first step of the post-translational modifications, which is followed by proteolytic cleavage of the three amino acid residues, AAX; and, finally, the cysteine residue exposed at the C-terminus is methylated. The Ras protein thus modified has a lipophilic C-terminus which interacts strongly with the plasma membrane.

The post-translational modifications described above involve three enzymes which control the farnesyl group transfer, the peptide hydrolysis and the methylation steps, respectively. An agent which suppresses the post-translational modifications by inhibiting one of the three enzymes is expected to be an effective anticancer drug. Along this line, therefore, there have been extensive studies to develop inhibitors of the enzymes for the post-translational modifications, particularly those of FPTase.

It has been observed that the FPTase isolated from mice is inhibited by compounds having the structural feature of the C-terminus of a Ras protein. Based on this observation, a number of peptide derivatives having a terminus sequence of CAAX have been synthesized and screened for their inhibitory activities (Y. Reiss, *Cell*, 62, 81(1990)). As a result, effective farnesyl-protein inhibitors designated as L-731,734 and L-731,735 have been developed by Merck Co.(N. E. Kohl et al., *Science*, 260, 1937(1993)). Meanwhile, a benzodiazepin derivative having good inhibitory activity has been discovered by Genentech Inc.(G. L. James et al., *Science*, 260, 1937(1993)). Also, Merck Co. has announced a developmental inhibitor designated L-744,822 which exhibits strong anti-tumor activity against carcinoma induced by transplanting ras oncogenes into nude mice (N. E. Kohl et al., *Nature Med.*, 1, 792(1995)).

There have also been many screening studies to identify natural products which may exhibit inhibitory activity against farnesyl-protein transferase. Among those reported to have such activity are: limonene, perillic acid and dihydroperillic acid of plant-origin; 10'-desmethoxystretonigrin isolated from actinomycetes; chaetomellic acid A and B isolated from the culture of *Chaetomella acutiseta;* and zaragozic acid A and B which were earlier recognized to be squalene synthase inhibitors. Other compounds reported to be FPTase inhibitors are pepticinnamins and diepoxybenz[a]anthracene (V. Manne et al., *Drug Devel. Res.*, 34, 121(1995); S. Omura et al., *Drug Future*, 19, 751(1994)).

Further, substances inhibiting the binding of Ras protein with plasma membrane exhibit activity in inhibiting the G2 to M phase progression in the cell cycle, due to its activity in inhibiting signal transmission in the cell (M. M. Feldkamo et al., *Oncogene*, 18, 7514(1999)). There have been other studies to develop controllers of the cell cycle with an aim to inhibit and treat cancers caused by abnormality of the cell cycle.

Angiogenesis, on the other hand, is a process of forming new blood vessels extending from existing veins and it occurs during the development and metastasis of cancer cells. As reported, this process may be facilitated by a factor called angiogenin isolated from the secretion of HT-29 human colon carcinoma cells (Vallee et al., *Biochemistry*, 24, 5480(1985)), while angiostatin, one of anti-angiogenic factors which suppress angiogenesis, inhibits the growth and metastasis of lung cancer cells (M. S. O'Relly et al., *Cell*, 79, 715(1994)). Examples of other anti-angiogenic factors are: alpha interferon which protects new born babies from lung angioma; antibodies of vascular endothelial growth factor; an anti-prostate cancer agent named genistein which is a natural product isolated from soy bean; platelet factor-4 and its peptide derivative; fumagillin and its derivative; ursolic acid; Herbimycin A; cartilage-derived inhibitor; and a synthetic compound named ovalicine.

As described above, there have been reported various FPTase, cell cycle and angiogenesis inhibitors. However there have continued to exist needs for new compounds having improved activity in said biological function. It is particularly desirable to develop an agent which is effective in inhibiting farnesyl-protein transferase, a progression of the cell cycle and angiogenesis. Such an agent would be especially useful for the prevention and treatment of various cancers and also for the treatment of angiogenesis-related diseases, e.g., rheumatism, diabetic retinopathy, chronic inflammation, retinitis and angioma.

SUMMARY OF THE INVENTION

Accordingly, it is an object of the present invention to provide a novel arteminolide derivative which can be effectively used in inhibiting farnesyl-protein transferase (FPTase), a progression of the cell cycle and angiogenesis.

It is another object of the present invention to provide a process for the preparation of said arteminolide derivative.

It is a further object of the present invention to provide a pharmaceutical composition containing an effective amount of said arteminolide derivative.

It is a still further object of the present invention to provide a method for inhibiting farnesyl-protein transferase (FPTase), a progression of the cell cycle and angiogenesis in a mammal.

In accordance with one aspect of the present invention, there is provided 8-acetylarteminolide of formula (I):

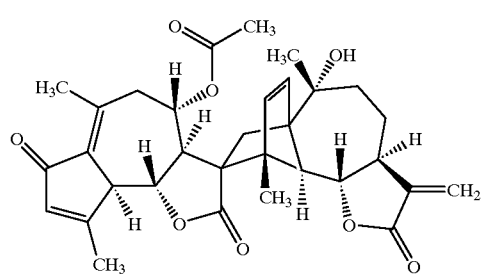

(I)

BRIEF DESCRIPTION OF THE DRAWINGS

The above and other objects and features of the present invention will become apparent from the following description of the invention taken in conjunction with the following accompanying drawings; wherein.

DETAILED DESCRIPTION OF THE INVENTION

Figure 1:
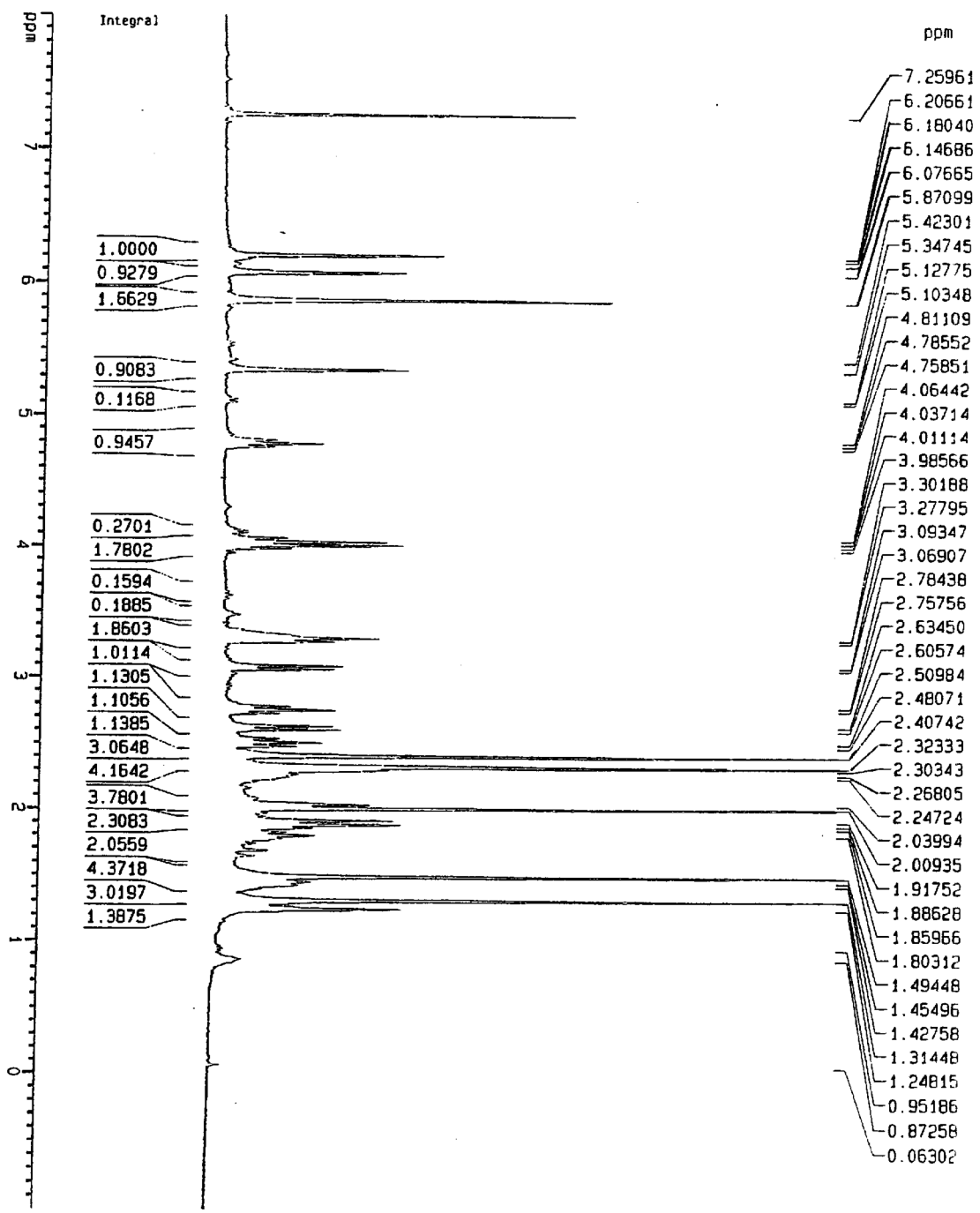
FIG. 1 shows the $^1$H-NMR spectrum of 8-acetylarteminolide.

The present invention discloses a novel arteminolide which is active in inhibiting farnesyl protein transferase, the progression of the cell cycle and angiogenesis.

The physicochemical properties of 8-acetylarteminolide are listed in Table 1.

TABLE 1

| Appearance | Non-color solid |
|---|---|
| Molecular formula | $C_{32}H_{36}O_8$ |
| Molecular weight | |

TABLE 1-continued

| measured: | 548.2480 |
|---|---|
| calculated: | 548.2410 |
| Melting Point | 110 |
| $[\alpha]_D$ (in MeOH) | −2.54 |
| Solubility | |
| Soluble: | alcohol, acetone, chloroform, DMSO |
| Insoluble: | hexane, $H_2O$ |

The inventive compound is extracted from the flower of *Artemisia sylvatica* MAXIMOWICZ by employing a suitable organic solvent and purified according to a common procedure, as described below.

The flower of *Artemisia sylvatica* MAXIMOWICZ is dried, pulverized and extracted with an organic solvent, e.g., a mixture of chloroform and acetone mixed in a weight ratio ranging from 2:1 to 1:2, preferably, 1:1, methanol and ethanol. The extract solution is filtered and concentrated under a reduced pressure. The concentrate is extracted with an organic solvent, e.g., methylene chloride and ethyl acetate, and the solvent was removed therefrom to obtain a crude extract containing arteminolides. This crude extract is refined by conducting a series of silica gel as well as C18 column chromatography using various combinations of solvents, e.g., hexane, ethylacetate, chloroform, methanol and water, as eluents to obtain an arteminolide fraction.

The arteminolide fraction thus obtained is subjected to high performance liquid chromatography using a mixture of water and methanol at a ratio ranging from 5:5 to 7:3 as an eluent to obtain fractions containing a novel arteminolide derivative which is designated 8-acetylarteminolide.

8-Acetylarteminolide obtained in accordance with the inventive process exhibits high inhibitory activity against farnesyl protein transferase, the concentration required for inhibiting farnesyl protein transferase by 50%($IC_{50}$) being about 1 μg/ml(1.8 μM). It is also active in inhibiting the $G_2$ to M phase progression in the cell division cycle, the concentration required for inhibiting the progression of the cell cycle by 50% being about 5 μg/ml.

Further, 8-acetylarteminolide has high inhibitory activity against angiogenesis, 10 μg/ml of the compound inhibiting angiogenesis by 60%.

The pharmaceutical composition of the present invention, which may be useful for the treatment of various cancers and angiogenesis-related diseases, comprises 8-acetylarteminolide as an active ingredient in combination with pharmaceutically acceptable excipients, carriers or diluents.

The pharmaceutical formulations may be prepared in accordance with any one of the conventional procedures.

In preparing the inventive composition, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the compositions may be in the form of tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include lubricating agents, wetting agents, flavoring agents, emulsifiers, preservatives and the like.

The compositions of the invention may be formulated so as to provide quick, sustained or delayed release of the active ingredient after their administration to a patient by employing any of the procedures well known in the art.

The pharmaceutical composition of the present invention can be administered by a variety of routes including oral, transdermal, subcutaneous, intravenous and intramuscular introduction. A typical daily dose of the active ingredient may range from about 1 to 50 mg/kg, preferably 2 to 15mg/kg body weight, more preferably 5 to 10 mg/kg body weight, and can be administered in a single dose or in divided doses. However, it should be understood that the amount of the active ingredient actually administered ought to be determined in light of various relevant factors including the condition to be treated, the chosen route of administration, the age and weight of the individual patient, and the severity of the patient's symptom; and, therefore, the above dose should not be intended to limit the scope of the invention in any way.

The following Examples are intended to further illustrate the present invention without limiting its scope; and the experimental methods used in the Examples can be practiced in accordance with the Reference Examples given herein below, unless otherwise stated.

Further, percentages given below for solid in solid mixture, liquid in liquid, and solid in liquid are on a wt/wt, vol/vol and wt/vol basis, respectively, unless specifically indicated otherwise.

EXAMPLE 1

Extraction and Purification of 8-acetylarteminolide from *Artemisia sylvatica* MAXIMOWICZ

*Artemisia sylvatica* MAXIMOWICZ growing in central parts of the Republic of Korea was harvested and dried. About 1.0 kg of the dried flowerof *Ariemisia sylvatica* MAXIMOWICZ was pulverized and 5 l of chloroform-acetone(1:1) mixture was added thereto. The resulting mixture was left standing at room temperature for 48 hours. The mixture was filtered and the filtrate was concentrated under a reduced pressure. The concentrated residue was extracted with 2 l of methylene chloride at room temperature for 1 hour and the resulting solution was concentrated under a reduced pressure to obtain a residue. The residue was dissolved in methylene chloride and subjected to silica gel column chromatography(silica gel(Merck, U.S.A., Art No.9385)), wherein a mixture of hexane and ethylacetate (9:1 to 3:7) was used as an eluent to remove non-polar substances, and then, a chloroform-methanol(1:9) mixture was used to elute a fraction having FPTase inhibitory activity. The fraction thus obtained was allowed to adsorb on a C18 column(Merck, U.S.A., LiChroprep RP-8) and a mixture of methanol and water was fed to the column while varying the methanol to water ratio from 6:4 to 8:1 to obtain a fraction having FPTase inhibitory activity.

The fraction thus obtained was subjected to thin layer chromatography(TLC plate: Merck silca gel 60 $F_{254}$) using a mixture of methanol and chloroform(5:95) as an eluent to obtain a fraction having FPTase inhibitory activity.

Finally, the resulting mixture was subjected to high performance liquid chromatography(column: Phenomenex, ultracab 10 ODS(250×21.2 mm)) wherein a mixture of water and methanol was used as an eluent while varying the water to methanol ratio from 5:5 to 7:3 to obtain 30 mg of pure 8-acetylarteminolide in the form of a white solid having the physicochemical properties shown in Table 1.

EXAMPLE 2

Structural Analysis of 8-acetylarteminolide

1) UV-Visible light analysis was carried out with UV-Vis spectrophotometer model UV-265(Shimadzu, Japan). The maximum absorption occurred at 254 (log $\epsilon$=4.20)nm.

2) IR studies conducted with model FTS-80, Bio-Rad Digilab Division: IR(KBr pellet) 3600, 2910, 1690, 1670, 1620, 1220, 1210, 1180, 910 and 880 $CM^{-1}$.

3) The molecular weight was determined with VG70-SEQ mass spectrometer(Vacuum Generator, UK) using the High-Resolution Electron Impaction(HREI)-MS method. The result showed the molecular formula: $C_{32}H_{36}O_8$(molecular weight: measured 548.2480, calculated 548.2410).

Figure 2:
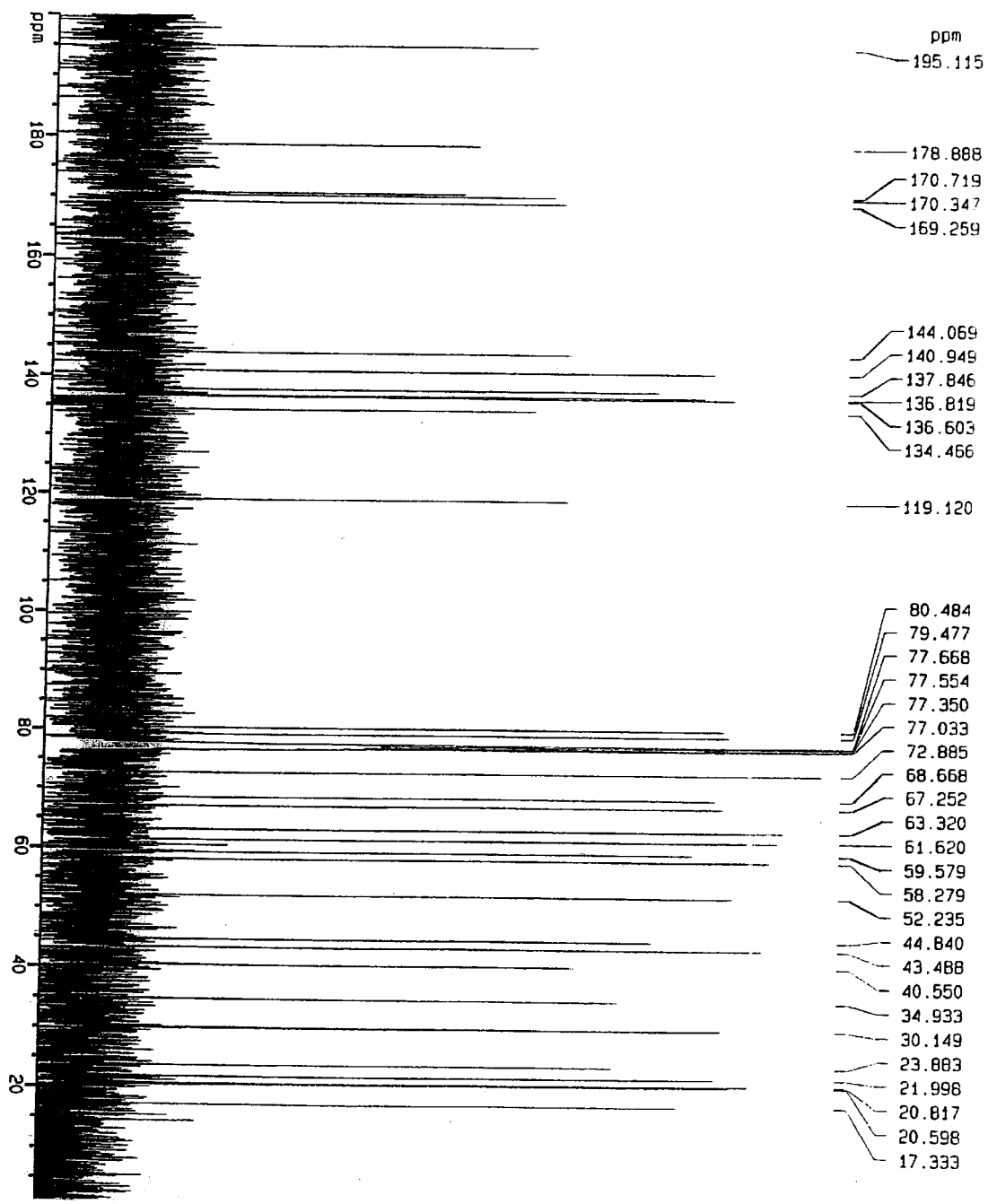
FIG. 2 displays the $^{13}$C-NMR spectrum of 8-acetylarteminolide.
Figure 3:
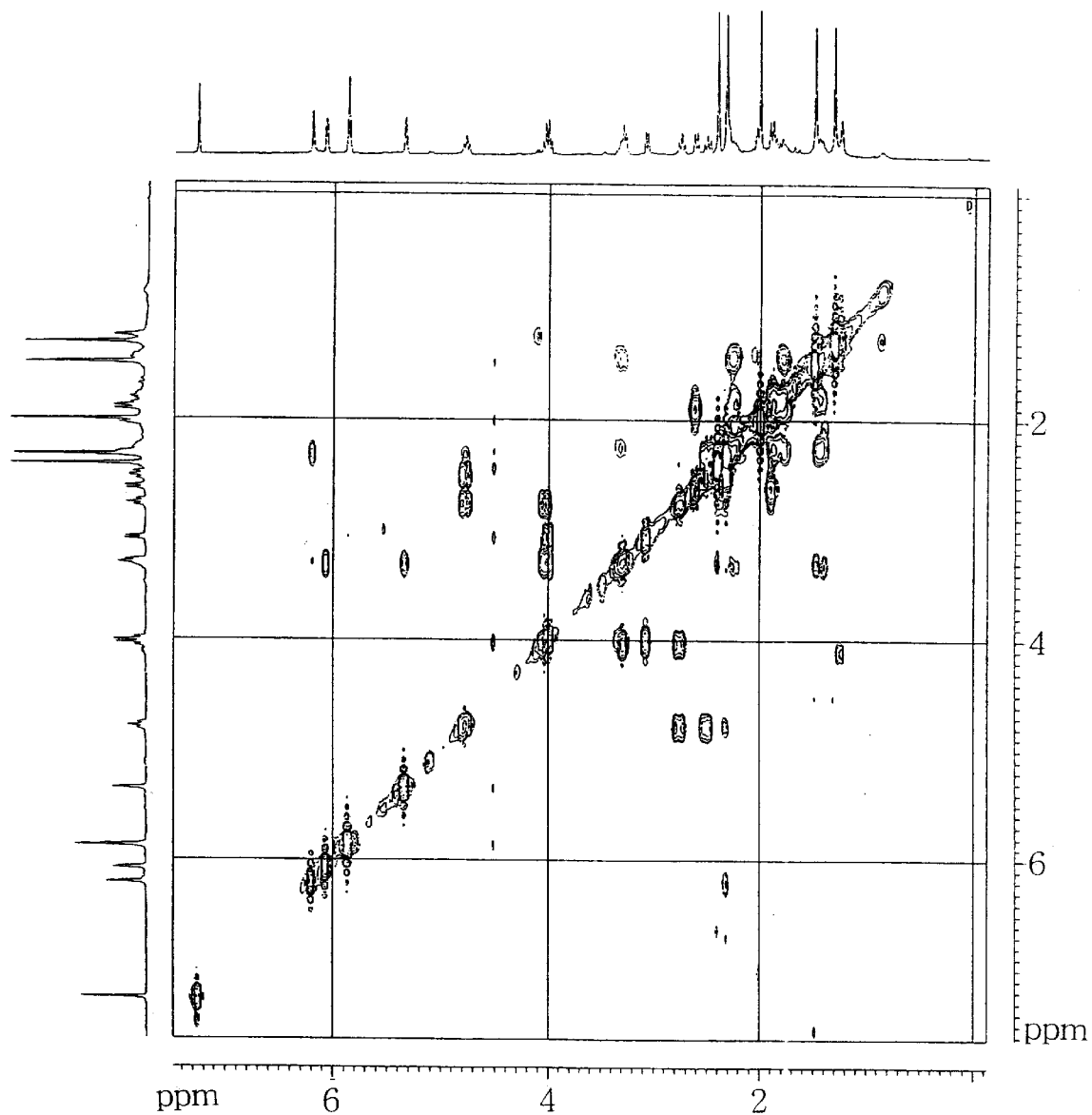
FIG. 3 represents the Cosy NMR spectrum of 8-acetylarteminolide.

4) NMR analyses were carried out with Varian 300 MHz, 500 MHz NMR. The H-NMR, C-NMR, HMQC NMR, HMBC NMR and COSY NMR data for 8-acetylarteminolide are shown in Table 2(see FIGS. 1, 2 and 3 for H-NMR, C-NMR and COSY NMR spectra of 8-acetylarteminolide, respectively).

Based on the above results, the structure of 8-acetylarteminolide was determined as in formula (I).

TABLE 2

| Atom | δC | δH | HMBC(C→H) | COSY |
|---|---|---|---|---|
| 1 | 134.46 | | 3, 5, 6, 9, 15 | |
| 2 | 195.11 | | 3 | |
| 3 | 136.60 | 6.20 (s) | 5, 14 | |
| 4 | 170.34 | | 3, 5 | |
| 5 | 52.23 | 3.28 (d, 9.8) | 3, 7 | 6 |
| 6 | 80.48 | 4.06 (t, 10.4) | 5, 7 | 5, 7 |
| 7 | 59.57 | 2.75 (t, 10.4) | 9 | 6, 8 |
| 8 | 68.66 | 4.78 (t, 10.4) | 7, 9 | 7, 9 |
| 9 | 44.84 | 2.50 (t, 12.4), 2.26 (m) | 15 | 8 |
| 10 | 144.06 | | 9 | |
| 11 | 61.62 | | 7 | |
| 12 | 178.88 | | 13 | |
| 13 | 40.55 | 2.57 (d, 11.6), 1.90 (d, 11.6) | 7 | |
| 14 | 20.59 | 2.32 (s) | | |
| 15 | 20.81 | 2.40 (s) | | |
| 16 | 169.25 | | 17 | |
| 17 | 23.88 | 2.00 (s) | | |
| 1' | 63.85 | | 2', 3', 6', 15' | |
| 2' | 132.59 | 5.79 (d, 5.6) | 5', 6' | 3' |
| 3' | 143.56 | 6.37 (d, 5.6) | 2', 14' | 2' |
| 4' | 57.92 | | 2', 3', 14' | |
| 5' | 66.86 | 1.98 (d, 9.9) | | 6' |
| 6' | 79.47 | 4.01 (t, 10.4) | 5' | 5', 7' |
| 7' | 44.05 | 3.07 (m) | 13' | 6', 8' |
| 8' | 24.34 | 2.20 (m), 1.46 (m) | | 9' |
| 9' | 35.53 | 1.83 (m), 1.77 (m) | 15' | 8' |
| 10' | 73.29 | | 9', 15' | |
| 11' | 141.37 | | 13' | |
| 12' | 170.71 | | 13' | |
| 13' | 120.12 | 6.09 (d, 3.4), 5.38 (d, 2.9) | | |
| 14' | 15.18 | 1.55 (s) | | |
| 15' | 30.51 | 1.28 (s) | | |
| 16' | 61.09 | 4.12 (q, 7.2) | 17' | 17' |
| 17' | 14.88 | 1.23 (t, 6.5) | | 16' |

EXAMPLE 3

Assay for Farnesyl-protein Transferase Inhibiting Activity

Farnesyl-protein transferase(FPTase) activity was determined in accordance with the scintillation proximity assay (SPA) method of Blown et al. described in *Cell*, 62, 1(1990) by using $^3$H-farnesyl pyrophosphate($^3$H-FPP) as a substrate.

First, the cerebrum of a white rat(male Sprague Dowley weighing 100–150 g) was washed with physiological saline solution and homogenized. The homogenized solution was centrifuged and partially purified by using Q sepharose fast flow column(Pharmacia, co.) to obtain famnesyl protein transferase(FPTase).

10 µl of 8-acetylarteminolide, 40 µl of FPTase obtained above, 10 µl of an assay buffer(50 mM Tris-HCl, pH 7.5, 25 mM MgCl$_2$, 2 mM KCl, 5 mM DTT, 5 mM Na$_2$HPO$_4$, 0.01% Triton X-100), 20 µl of diluted $^3$H-FPP and 20 µl of biotin-lamin B peptide were mixed together and the resulting mixture was reacted at room temperature for 30 minutes. 150 µl of SPA bead/stop reagent solution(Amersham, Inc. UK) was added to the mixture and the enzymatic activity was determined by examining the extent of biotin-lamin B peptide farneslyation, expressed by unit of count per minute (CPM), with a liquid scintillation counter.

The FPTase inhibiting activity was then calculated in accordance with the following equation:

$$\text{Degree of Inhibition}(\%) = 100 \times \left[1 - \frac{\text{CPM(sample)} - \text{CPM(blank)}}{\text{CPM(control)} - \text{CPM(blank)}}\right]$$

wherein the blank represents the value obtained without the use of the enzyme and 8-acetylarteminolide, and the control, in the absence of 8-acetylarteminolide.

Consequently, the IC$_{50}$ value of 8-acetylarteminolide calculated from the degree of inhibition was 1 µg/ml(1.8 µM).

EXAMPLE 4

Assay for the Cell-cycle Inhibiting Activity of 8-acetylarteminolide

Human breast cancer cell line MCF-7(ATCC HTB-22) was divided into 7.5 ml portions of RPMI1640 culture medium(GIBCO BRL) kept in T25 flasks and incubated at 37° C. under an atmosphere containing 5% CO$_2$ for 12 hours. Added to the cell cultures of one group of flasks was 7.5 µl of DMSO solution containing 5 mg/ml of 8-acetylarteminolide obtained in Example 1, while 7.5 µl of pure DMSO was added to the cultures of another group of flasks as a control, followed by incubation at 37° C. under an atmosphere containing 5% CO$_2$ for 12, 24 and 36 hours, respectively.

To examine the activity of inventive compound in inhibiting the progression of the cell cycle, each of the cultures was treated with trypsin and centrifuged at 200×g for 5 minutes, and then, the cell precipitate was washed twice with cold PBS. 3 ml of 70% ethanol was added thereto and the resulting mixture was left standing at −20° C. for 12 hours to fix the cell. The resulting mixture was centrifuged at 200×g for 5 minutes and the cell precipitate was washed twice with PBS to remove remaining ethanol. Added to the cell precipitate in sequence were 1 ml of PBS and 50 µl RNase A solution(100 µg/ml). The mixture was reacted at 37° C. for 30 minutes and 10 µl of PBS containing 1 mg/ml of propidium iodide was added thereto.

The cell cycles of 20,000 stained cells were analyzed by using Becton-Dickinson FACS Calibur and Becton-Dickinson Modifit cell-cycle analysis program.

The result was summarized in Table 3.

TABLE 3

| Times (hours) | | % of cells | | |
|---|---|---|---|---|
| | | G$_0$/G$_1$ phase | S phase | G$_2$/M phase |
| 12 | Control | 48.17 | 36.29 | 15.53 |
| | 8-acetylarteminolide | 47.59 | 34.35 | 18.06 |
| 24 | Control | 55.06 | 42.13 | 2.8 |
| | 8-acetylarteminolide | 47.49 | 24.54 | 27.97 |
| 36 | Control | 63.24 | 26.99 | 9.76 |
| | 8-acetylarteminolide | 73.2 | 7.01 | 19.79 |

As shown in Table 3, the addition of 8-acetylarteminolide induce a marked increase of cells in the G$_2$/M phase at 24 hours or 36 hours of exposure, with a concomitant reduction of cells in the S phase, while the proportion of cells in G$_0$/G$_1$ phase did not change significantly. Compared to the control cells, the percentages of cells in the G$_2$/M phase were 10-fold higher at 24 hours and two-fold higher at 36 hours. This result shows that 8-acetylarteminolide acts on the cells to accumulation at the G$_2$/M phase of the cell cycle and also inhibits the cellular proliferation of MCF-7 cells via such G$_2$/M phase arrest of the cell cycle.

EXAMPLE 5

Assay for Angiogenesis-suppressing Activity of 8-acetylarteminolide

Angiogenesis was determined in accordance with the chorioallantoic membrane(CAM) assay method described in Kusaka et al., *Biochem. Biophy. Res. Comm.*, 174, 1070 (1991), using fertilized chicken eggs.

1) Day 1(0 Day-embryo)

A fertilized chicken egg(Pulmuwon co., Korea) was incubated at 37–38° C. and a humidity of more than 90%. Here, 0 day-embryo means that the fertilized egg had been stored at 18° C. for less than 4 days since laying.

2) Day 3(2 Day-embryo)

The pointed end of the fertilized egg was scratched with a knife, laid horizontally, the scratched site was punctured with a 5 ml syringe and 2 ml of albumin was extracted from the fertilized egg. The puncture hole was then sealed with a glass-tape. The fertilized egg, positioned such that the sealed hole was at the bottom, was incubated under the same condition described above.

3) Day 4(3 Day-embryo)

The end of the fertilized egg where the air sac is located, i.e., the end opposite to the hole site was opened, a window having a diameter of 2–3 cm was installed therein, the window was sealed with a glass-tape, and the incubation was resumed.

4) Day 5(4.5 Day-embryo)

By this time, a CAM of 2–5 mm diameter had developed. 8-Acetylarteminolide was dissolved in ethanol to a concentration of 10 µg/ml, 10 µl of the solution was dropped on quartered Thermanox coverslip(Nunc, Co.,) and dried in a clean bench. The sealing glass-tape was removed, the treated Thermanox coverslip obtained above was laid on the CAM and then sealed with a glass-tape. All tools used in the above procedure were pre-sterilized sterilized with 70% ethanol.

5) Day 7(6.5 Day-embryo)

The sealing glass-tape was removed. 1 ml of Intralipose (fat emulsion, Green Cross co., Korea) was taken in a syringe, removed air bobbles therefrom and injected into the area below the CAM.

Angiogenesis suppressing activity was then calculated in accordance with the following equation:

$$\text{Degree of Suppression (\%)} = 100 \times \frac{\text{number of eggs showing angiogenesis suppression at } CAM}{\text{number of eggs tested}}$$

10 μg/ml of 8-acetylarteminolide suppressed angiogenesis by 60%.

While the embodiments of the subject invention have been described and illustrated, it is obvious that various changes and modifications can be made therein without departing from the spirit of the present invention which should be limited only by the scope of the appended claims.

What is claimed is:

1. A method for inhibiting farnesyl-protein transferase (FPTase), a progression of the cell cycle and angiogenesis in a mammal, which comprises administering an effective amount of 8-acetylarteminolide of formula (I) thereto:

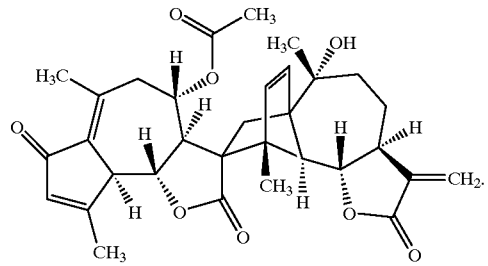

(I)

* * * * *